United States Patent
George et al.

(10) Patent No.: US 6,773,439 B2
(45) Date of Patent: Aug. 10, 2004

(54) STERILIZING INSTRUMENT

(76) Inventors: Samuel George, 4 Ronneby Close, Weybridge, Surrey (GB), KT13 9SB; Yusuf Abrahams, "Lake View", Sandy Lane, Northwood, Middlesex (GB), HA6 3ES ( * ) Notice: Subject to any disclaimer, the term of this patent is extended or adjusted under 35 U.S.C. 154(b) by 204 days.

(21) Appl. No.: 10/085,216

(22) Filed: Feb. 28, 2002

(65) Prior Publication Data

US 2002/0143353 A1 Oct. 3, 2002

Related U.S. Application Data (63) Continuation of application No. PCT/GB00/03370, filed on Aug. 31, 2000.

(30) Foreign Application Priority Data

Sep. 1, 1999 (GB) .............................. 9920675

(51) Int. Cl.[7] .............................................. A61B 17/00
(52) U.S. Cl. ....................................................... 606/141
(58) Field of Search ................................ 606/141, 140, 606/151, 157, 158, 205–208

(56) References Cited

U.S. PATENT DOCUMENTS

| | | |
|---|---|---|
| 3,989,049 A | 11/1976 | Yoon |
| 4,174,715 A | 11/1979 | Hasson |
| 4,822,348 A | 4/1989 | Casey |
| 5,334,209 A | 8/1994 | Yoon |
| 5,383,471 A | 1/1995 | Funnell |
| 5,788,716 A | 8/1998 | Kobren et al. |
| 5,922,002 A | 7/1999 | Yoon |
| 5,972,002 A * | 10/1999 | Bark et al. ................... 606/141 |
| 5,980,537 A * | 11/1999 | Ouchi ......................... 606/140 |

* cited by examiner

*Primary Examiner*—Kevin T. Truong
(74) *Attorney, Agent, or Firm*—Lerner, David, Littenberg, Krumholz & Mentlik, LLP (57) ABSTRACT

A laparoscopic sterilization instrument comprises an excisor for excising a portion of a patient's oviduct and a receptacle for holding the excised oviduct portion until the instrument has been withdrawn from the patient's abdomen. The excised oviduct portion constitutes a full circumference biopsy that can be examined to confirm proper performance of the sterilization procedure, for the protection of patient and physician alike. The instrument includes first and second elongate parts attached to each other for relative movement parallel to their longitudinal axes to operate the excisor means. The first part is a rod and the second part is a sleeve within which the rod can move, the rod sliding longitudinally within the sleeve. The instrument is operable by a physician to work the excisor means and an applicator for applying a clip in a single action.

29 Claims, 6 Drawing Sheets

STERILIZING INSTRUMENT

CROSS-REFERENCE TO RELATED APPLICATIONS

This application is a continuation of International Application No. PCT/GB00/03370, filed on Aug. 31, 2000 and published in English under International Publication No. WO 01/15610 on Mar. 8, 2001, the entire disclosure of which is incorporated herein by reference.

FIELD OF THE INVENTION

This invention relates to a surgical instrument for sterilizing a patient, and especially to an instrument adapted to cut and occlude the Fallopian tubes, or oviducts, of a female patient.

BACKGROUND OF THE INVENTION

Much misery is caused by unwanted pregnancy. It presents the unpalatable alternatives of abortion with its emotional turmoil and social cost or, if the parent(s) are unwilling to terminate the pregnancy for religious or other reasons, the imposition of an unexpected child. The life of the child and its parents can be ruined, with the child suffering from a lack of love and support and the relationship between its parents coming under strain due to emotional and financial problems. These problems can be all the worse if the child is physically or mentally handicapped.

There are also medical reasons for avoiding unwanted pregnancy. The parents' genetic makeup may predispose a child to be physically or mentally handicapped, or the mother may harbour infection such as HIV that might be passed on to the child. The parent(s) may be mentally or physically unable to look after a child, or the mother may be so ill that continuation or even termination of a pregnancy presents a serious risk to her.

For all of these reasons, reliable birth control or family planning is one of the major objectives of medical science. A large part of this effort relates to sterilization, which is now the most commonly-used method of family planning in the world. In 1990, for example, more than 190 million married women of reproductive age relied on sterilization of themselves or their partners for contraception. This represents 22% of married women of reproductive age in developing countries and 11% in developed countries. Indeed, in the US, sterilization has become the most commonly used method of contraception among married couples. Sterilization is intended to be permanent: reversal surgery is available, but it can be difficult and can never guarantee to restore fertility.

In the case of a female, sterilization generally involves occluding and optionally also cutting the Fallopian tubes, or oviducts, that convey ova from the ovaries to the cavity of the uterus. The term oviducts will be used hereinafter for convenience. Briefly, the oviducts are situated in the free margin of the broad ligament that extends outwardly in a layered web-like manner from the sides of the uterus. The part of the broad ligament that supports the oviducts is known as the mesosalpinx. The layers of the broad ligament also embrace the two round ligaments that extend forwardly, outwardly and downwardly from the uterus.

There are several sterilization techniques involving occlusion of the oviducts, notably:

(i) Ligation with partial salpingectomy, in which the oviducts are tied with suture material and cut, most commonly by tying off a small loop of the oviduct and then cutting through the loop. This procedure is performed through an abdominal incision and so is most often used when sterilization procedures are performed postpartum or if laparoscopic surgery is not possible because of obesity or inaccessibility, for example due to pelvic adhesions.

(ii) Coagulation or cautery, in which electrical current is used to block or divide the oviducts. This procedure is effective, but brings a risk of thermal injury to nearby tissues such as so-called bowel burn, as discussed by Thompson et al in *Obstetrics & Gynaecology* May 1973, Vol. 41, No. 5, at page 669 et seq.

(iii) The application of a silicone or Silastic band such as a Falope ring in which, using a special applicator, the surgeon forms a loop in the oviduct and stretches a small silicone ring to slip it over the loop. The ring thus compresses and occludes the oviduct at the neck of the loop, strangling the portion of oviduct that forms the loop. The procedure is discussed at length by Levinson et al in *Obstetrics & Gynaecology* October 1976, Vol. 48, No. 4, at page 494 et seq., and by Yoon et al in *The Journal of Reproductive Medicine* Jan. 15, 1977, Vol. 127, No. 2 at page 109 et seq., in the *American Journal of Obstetrics & Gynaecology* August 1979, Vol. 23, No. 2 at page 76 et seq., and in *The Journal of Reproductive Medicine* August 1979, Vol. 23, No. 2 at page 76 et seq.

(iv) The application of a clip to the isthmic part of the oviduct to compress and thus occlude the oviduct, most notably the Hulka-Clemens or Hulka spring clip most commonly used in the US and the Filshie clip most commonly used in Europe. Initial experience of the Hulka clip is discussed by Hulka et al in the *American Journal of Obstetrics & Gynaecology*, Jul. 1, 1973, Vol. 116, No. 5 at page 715 et seq. Similar experience of the Filshie clip is discussed by Filshie et al in the *British Journal of Obstetrics & Gynaecology* June 1981, Vol. 88, pp. 655–662. There are other types of occlusive clip, such as the recently-introduced Cambridge clip.

Apart from ligation with partial salpingectomy, the above procedures are apt to be performed laparoscopically. Laparoscopic female sterilization is popular because of its short recovery time and relatively low complication rate.

As female sterilization is invariably performed upon those for whom pregnancy is deemed to be undesirable or unsafe, it follows that the probable consequence of a failed sterilization—an unexpected pregnancy—is all the more damaging. Failed sterilization also involves an increased risk of ectopic pregnancy, which presents a very direct threat to the patient's health: as many as one third of sterilization failures involve ectopic pregnancy. Unsurprisingly, therefore, failed sterilization is one of the major reasons for law suits against gynaecologists and obstetricians, in some countries accounting for one third of all such cases.

The prospect of damages and legal costs coupled with the increasingly hostile climate of litigation for medical negligence adds to the stress of the physician's life and escalates the cost of medical negligence insurance. Nor should the professional impact of a medical negligence claim be forgotten: an accusation of negligence based upon a failed sterilization can be as damaging for the physician's professional career as it is for the lives of those most directly affected by an unwanted pregnancy.

Sterilization can fail for various reasons, but where an occlusive device is employed, failure can usually be attributed to improper application of the occlusive device. A clip should be applied so that it completely compresses and occludes the oviduct, for which purpose the clip should be placed on the distal isthmus end of the oviduct (3 cm from the cornual end of the uterus) at precisely 90° to the longitudinal axis of the oviduct, with one side of the oviduct lying against the hinge of the clip and the clip embracing part of the mesosalpinx on the other side of the oviduct. If these objectives are not fully met, the clip might not properly occlude the oviduct. Analogous problems are encountered with Falope rings, as explained in the abovementioned 1979 paper by Yoon et al in *The Journal of Reproductive Medicine*. It is even possible for the clip or ring to be applied to the wrong structure entirely, for example to the round ligament that can quite easily be confused with the oviduct during laparoscopic procedures.

Both clips and rings can fail if the oviducts are thicker than normal for whatever reason. Clips may be unable to cross the full thickness of the oviduct, and the loop of oviduct formed by a ring applicator may be severed by the force used to pull the loop into the applicator. Rings also fail sometimes because the applicator does not form a proper loop in the oviduct, especially when the loop is too small. In that instance, any stretching movement of the oviduct will cause the ring to slip.

Not all failed sterilizations are the physician's fault. Clips or rings can slip from an oviduct even if they are properly applied, although this is a difficult situation to verify as a misplaced clip or ring could, of course, merely indicate failure by the physician properly to apply the clip or ring to the oviduct. The benefit of any such doubt is not often exercised in the physician's favour, bearing in mind that the mere existence of doubt can be sufficient grounds for a successful negligence claim or at least lead to an expensive settlement. It is also known that a clip or ring can migrate from the oviduct when the crushed tissue at the site of its application undergoes necrosis and the oviduct divides into stumps, the clip or ring then possibly either lodging in nearby tissue or, in very rare cases, being expelled from the body through the vagina or rectum. It is unlikely that a patient would regain fertility in the event of such migration but it clearly presents a risk of complications such as infection and tissue damage.

Such is the risk of litigation that some gynaecologists and obstetricians make video tapes or still pictures of each and every sterilization procedure that they perform, so that if ever challenged, they have at least some evidence to confirm that the procedure was done properly. These images are kept in the patient's records for future reference but must be kept for several years, at least until the patient's reproductive capacity has ended with age.

It is against this background that the present invention has been made.

SUMMARY OF THE INVENTION

The invention resides in a laparoscopic sterilization instrument comprising excision means for excising a portion of a patient's oviduct and a receptacle for holding the excised oviduct portion until the instrument has been withdrawn from the patient's abdomen. The excised oviduct portion constitutes a full circumference biopsy that can be examined to confirm proper performance of the sterilization procedure, for the protection of patient and physician alike. The invention also resides in methods for use of the instrument.

In the preferred embodiment to be described, the instrument includes first and second elongate parts defining longitudinal axes and distal and proximal ends, the parts being attached to each other for relative movement parallel to their longitudinal axes to operate the excision means. More specifically, in that embodiment, the first part is a rod and the second part is a sleeve within which the rod can move, the rod suitably moving by sliding within the sleeve.

The excision means of the instrument preferably comprises at least one excision blade on at least one of the parts and means associated with the receptacle for gripping the oviduct and moving the gripped oviduct across the excision blade during said relative movement between the parts. Conveniently, the movement of the gripped oviduct across the excision blade takes place in a proximal direction. Where the first part is a sleeve, as is preferred, the excision blade is suitably associated with the distal end of the sleeve to cut the gripped oviduct during proximal movement of the rod. For example, the excision blade can be defined by at least one sharp-edged cut-out in the distal end of the sleeve.

Advantageously, the instrument further includes means attached to one of the parts being co-operable with the other of the parts to limit relative movement of the parts. Movement can be limited along (or in parallel to) and about the longitudinal axes of the parts.

As sterilization usually involves the application of an occlusive device such as a clip or ring, the instrument preferably further includes application means for applying an occlusive device to the oviduct. Where the occlusive device is a ring, that ring is advantageously held on a first part of the instrument and the application means operates by relative movement of the second part of the instrument to move the ring off the first part and onto the oviduct. Where these parts are a rod and a sleeve as aforesaid, a shoulder or ramp on the distal end of the sleeve suitably abuts the ring to force the ring off the distal end of the rod during proximal movement of the rod relative to the sleeve.

It is greatly preferred that the instrument is operable by a physician to work the excision means and the application means in a single action. In that case, it is also preferred that the application means operates before the excision means during that action. This affords the physician every opportunity to check and if necessary repeat any aspect of the procedure before the oviduct is cut.

Efficiently to receive the oviduct, the receptacle is preferably disposed transversely with respect to the longitudinal axis of the instrument. In preferred embodiments, the receptacle is defined between co-operating formations in opposed jaws provided at the distal end of the instrument. These formations are preferably troughs extending across the jaws, that co-operate to define the receptacle when the jaws are closed.

For reliable grip on the oviduct during the procedure, barb or tooth means are preferably associated with at least one trough, being adapted to resist removal of the oviduct from the receptacle or the trough.

For reliability in forming a loop of the oviduct ready for application of an occlusive device and then excision, the trough is separated from the distal extremity of the jaw. The separation is preferably at least 1 cm. To obtain a usefully large biopsy sample of the oviduct, the trough is preferably at least 5 mm long.

To achieve easy separation of the oviduct from the supporting mesosalpinx, blade means may be associated with the jaws. Such blade means are disposed distally with respect to the receptacle, and are operable on closure of the jaws to cut into or through the mesosalpinx. The blade means comprises a blade on at least one jaw, the blade being disposed transversely with respect to the longitudinal axis of the instrument, and means on the other jaw co-operable with the blade.

Conveniently, the jaws of the instrument can be opened by an actuating link operable from the proximal end of the instrument. The jaws can be opened by distal movement of this actuating link and hence can be closed by proximal movement of the actuating link. In a particularly elegant arrangement, continued proximal movement of the actuating link operates the excision means to excise the portion of oviduct held by the receptacle in the jaws.

To keep the jaws closed until they are required to be open, the jaws are preferably biased shut by spring means. The spring means suitably biases the actuating link proximally.

For ease of operation, manipulation means of the instrument preferably include means on the actuating link adapted for co-operation with the operator's thumb and means on an opposed part of the instrument adapted for co-operation with fingers of the operator's same hand. These manipulation means are suitably a ring on the actuating link and a flange on the opposed part of the instrument.

Within the inventive concept, the invention may also be expressed as a laparoscopic sterilization instrument including application means for applying an occlusive device permanently to occlude a patient's oviduct, and means for excising a full circumference biopsy of the oviduct during the sterilization procedure. This instrument is preferably adapted to form a loop in the oviduct, to apply the occlusive device to the neck of the loop, and to excise the biopsy from the portion of oviduct within the loop. It is further preferred that the instrument is adapted to leave free end sections of the portion of the loop that remains after excision of the biopsy. These features combine to facilitate a simple procedure that gives reliable results for the reproductive life of the patient.

The instrument as defined herein can be supplied in a sterile pack with an occlusive device already fitted. In that case, the instrument is suitably adapted for single use only.

The invention extends to an occlusive clip or ring for application to a patient's oviduct during a sterilization procedure, wherein the clip or ring is a resilient disc defining a face, the disc being penetrated by at least one slit that extends almost entirely across the face of the disc to define a central opening flanked by wall portions of different thickness. The slit is preferably rectilinear and there can be first and second intersecting slits, which are preferably symmetrically intersecting and orthogonally disposed to define a cross-shaped central opening. The invention also encompasses a clip or ring for application to a patient's oviduct during a sterilization procedure, the clip or ring including means for cutting the oviduct and means for occluding the oviduct.

BRIEF DESCRIPTION OF THE DRAWINGS

In order that the invention can be more readily understood, reference will now be made, by way of example, to the accompanying drawings in which.

DETAILED DESCRIPTION

Figure 1:
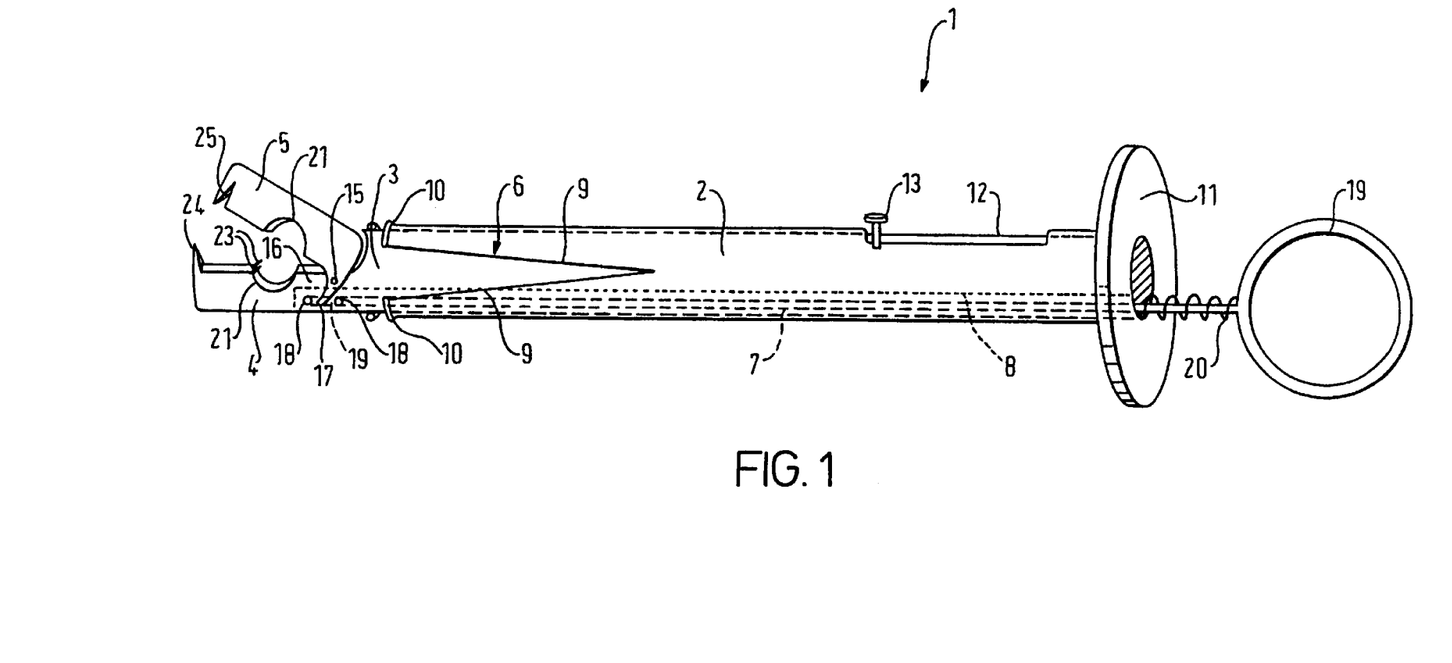
FIG. 1 is a side, elevational, partially schematic view of an instrument in accordance with the present invention.

Referring to FIG. 1 of the drawings, a sterilization instrument 1 comprises an elongate tubular sleeve 2 of circular cross section surrounding a rod 3 of generally circular cross section that is a sliding fit within the sleeve 2. As will be explained, the distal end of the rod 3 includes jaws 4, 5 for engaging an oviduct and the distal end of the sleeve 2 includes cutting means 6 co-operable with the jaws 4, 5 to cut a full circumference biopsy of the engaged oviduct as the rod 3 retracts in a proximal direction within the distal end portion of the sleeve 2. The biopsy can then be archived or sent for histological confirmation and filing.

The instrument 1 is not drawn to scale in the Figures but it is envisaged that the rod 3 would be about 30 cm in overall length, that the sleeve 2 would be about 26.5 cm in overall length and that the major portion of the sleeve 2 would be no more than 8 mm wide. These dimensions are not in themselves essential but they reflect laparoscopic practice around the world, being chosen to suit the typical size of a trochar and canula through which the instrument 1 will be introduced into the patient's abdominal cavity in well-known manner.

The rod 3 slides proximally within the sleeve 2 when the operating physician pulls an actuating link 7 carried by the rod 3; when pulled in this way to effect proximal movement of the rod 3, the actuating link 7 also closes the jaws 4, 5. To this end, the actuating link 7 lies within a groove or bore 8 extending longitudinally along the rod 3 in parallel to its longitudinal axis. Where a groove is employed instead of a bore, the sleeve 2 around the rod 3 suitably confines the link 7 within the groove. Longitudinal sliding movement of the actuating link 7 along the groove or bore 8 can take place with respect to the rod 3 in the distal and proximal directions as appropriate to open or close the jaws 4, 5, as will also be explained.

The cutting means 6 at the distal end of the sleeve 2 consists of a pair of proximally-converging cut-outs 6 that are in mutual diametrically opposed symmetrical relation about the cross section of the sleeve 2. Only one cut-out 6 is shown in FIGS. 1 to 8 because the other cut-out 6 of the pair is hidden on the other side of the instrument 1, but both cut-outs 6 are visible in the plan views of FIGS. 9 and 10 to which reference will be made in due course. Each cut-out 6 has two proximally-converging straight edges 9 in V formation that are chamfered in cross section to define sharp cutting edges. The distal end portion of the sleeve 2 that extends between the cut-outs 6 is thickened to form a ramp 10 that is preferably integral with the sleeve 2, but could alternatively be an attachment to the sleeve 2.

The proximal end of the sleeve 2 terminates in an annular flange 11 that extends radially from the proximal end of the sleeve 2 to a diameter of about 5 cm, although this dimension is not critical.

Near the flange 11 at the proximal end, the wall of the sleeve 2 is penetrated by a longitudinally-extending slot 12 of, for example, 4 cm in length that receives a screw 13 screwed into a threaded hole in the rod 3 extending orthogonally to the longitudinal axis of the rod 3. The head of the screw 13 lies outside the sleeve 2 and the screw 13 is a sliding fit within the slot 12, one purpose of the screw 13 being to limit axial movement of the rod 3 within the sleeve 2 by abutment with the ends of the slot 12. The screw 13 is therefore positioned with respect to the rod 3 and the sleeve 2 in such a way that when the proximal end of the rod 3 is level with the flange 11 at the proximal end of the sleeve 2, the screw 13 abuts the distal end of the slot 12 to prevent further movement of the rod 3 distally with respect to the sleeve 2. Conversely, when the distal end portion of the rod 3 has been retracted into the distal end portion of the sleeve 2 to an extent sufficient to cut the desired biopsy from the oviduct, the screw 13 abuts the other, proximal end of the slot 12 to prevent further proximal movement of the rod 3 with respect to the sleeve 2. The screw 13 running within the slot 12 also prevents any significant angular relative movement between the rod 3 and the sleeve 2 about their mutual longitudinal axis.

The jaws 4, 5 at the distal end of the rod 3 comprise a fixed jaw 4 and a movable jaw 5 hinged with respect to the fixed jaw 4. For this purpose, the movable jaw 5 has hinge portions 14 depending from its proximal end and is fixed to the rod 3 by a transverse hinge pin 15 that extends through the hinge portions 14 and through the part of the rod 3 that lies between the hinge portions 14. The rod 3 is cut away at its sides at the region 16 around the hinge pin 15 to accommodate the hinge portions 14 of the movable jaw 5 in a flush-fitting manner that enables the jaws 4, 5 to retract into the sleeve 2 when closed.

Each hinge portion 14 extends into a crank arm 17 that is embraced by a pair of parallel transverse arms 18 at the distal end of the actuating link 7. The transverse arms 18 of the actuating link 7 protrude through a short longitudinal through-slot 19 in the rod 3 adjacent the hinge pin 15, to transmit to the crank arms 17 of the movable jaw 5 any movement of the link 7 with respect to the rod 3. It is this movement, depending upon its direction, that opens and closes the jaws 4, 5 by moving the movable jaw 5 away from or towards the fixed jaw 4.

Figure 2:
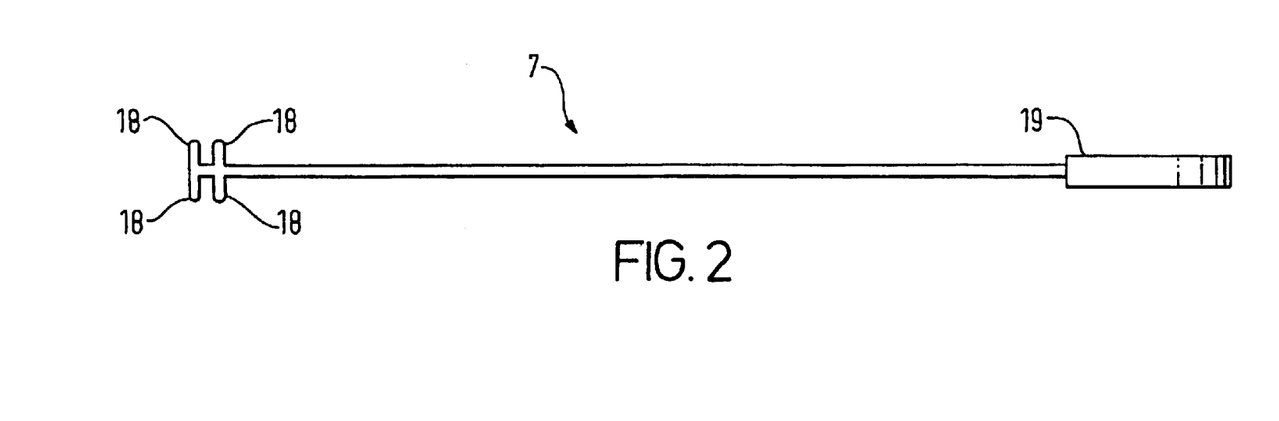
FIG. 2 is a side, elevational view of an actuating link used in the instrument shown in FIG. 1.

Reference is also made at this juncture to the plan view of the actuating link 7 in FIG. 2 of the drawings, in which the transverse arms 18 can be seen as an I-shaped formation at the distal end of the link 7. The proximal end of the actuating link 7 is defined by a circular actuating ring 19 designed to admit the operating physician's thumb. So, when the operating physician uses the actuating ring 19 to pull the actuating link 7, thus moving the link 7 proximally with respect to the rod 3 in parallel to the longitudinal axis of the rod 3 and also pulling the rod 3 proximally within the sleeve 2, the jaws 4, 5 close more tightly. Conversely, the jaws 4, 5 open when the actuating link 7 is moved distally with respect to the rod 3.

A coil spring 20 disposed around the proximal part of the actuating link 7, as seen in FIG. 1, acts in compression between the actuating ring 19 and the proximal end of the rod 3 to bias the link 7 proximally with respect to the rod 3 and thereby to hold the jaws 4, 5 closed. The jaws 4, 5 remain closed until the operating physician applies pressure to the actuating ring 19 in the distal direction, against the bias of the spring 20, to open the jaws 4, 5. The screw 13 abuts the distal end of the slot 12 in the sleeve 2 to prevent distal movement of the rod 3 with respect to the sleeve 2 as the jaws 4, 5 are opened in this way.

The fixed jaw 4 is defined by a cut-away portion at the distal end of the rod 3 that accommodates the movable jaw 5 so that, when closed against the fixed jaw 4, the movable jaw 5 can retract within the distal end of the sleeve 2 along with the rest of the rod 3. To this end, the cut-away portion is partially defined by a central generally planar longitudinal cut through the rod 3, and the movable jaw 5 mirrors the shape and size of the cut-away portion. In the embodiment described, the cut-away portion and hence the movable jaw 5 that fits into that cut-away portion are about 3 cm in length.

Both the fixed jaw 4 and the movable jaw 5 further comprise mirror-image transverse troughs 21 of generally semi-circular or part-elliptical section that extend from one side of the rod 3 to the other, orthogonally to the longitudinal axis of the rod 3. When the jaws 4, 5 are closed, the troughs 21 come together to define a generally circular or elliptical through-hole extending transversely through the rod 3 in line with the cut-outs 6 at the distal end of the sleeve 2. As will be explained, this through-hole is intended to receive a portion of the oviduct for biopsy excision, and so will be referred to hereinafter as a receptacle 22.

In the example described, the troughs 21 are about 1 cm wide and are disposed centrally with respect to the length of the jaws 4, 5, the distal edge of each trough 21 thus being about 1 cm from the distal extremity of its respective jaw 4, 5 while the proximal edge of the trough 21 is about 1 cm from the proximal end of its respective jaw 4, 5. The troughs 21 and thus the receptacle 22 that they define are the same length as the width as the rod 3 at its distal end, that is to say, about 5 mm in the embodiment described.

The distal edge of the trough 21 in the fixed jaw 4 has proximally-inclined teeth or barbs 23. The distal extremity of the fixed jaw 4 also has a sharp triangular blade 24 and the distal extremity of the movable jaw 5 has a complementary sharp-edged recess 25 that receives the blade 24 in a scissor action as the jaws 4, 5 close.

The purpose of the various features of the instrument 1 and its general operation will be apparent from the description of its use that now follows with reference to FIGS. 3 to 10.

Figure 3:
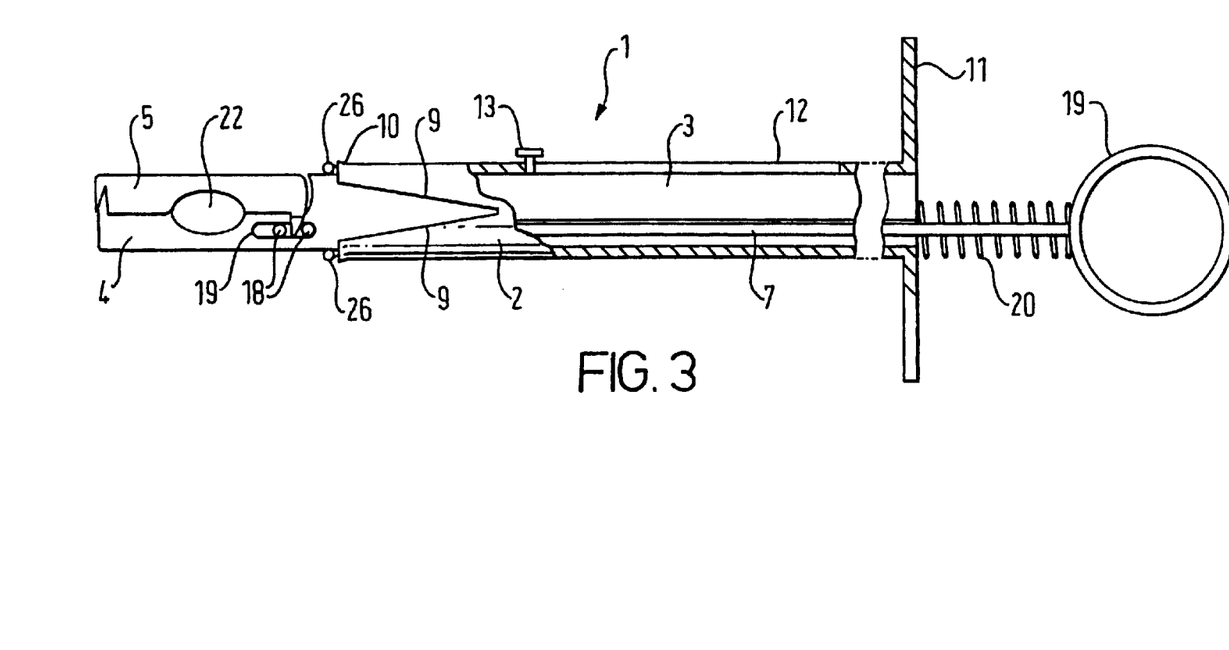
FIG. 3 is a side, elevational, partially schematic, partially sectional view of the instrument shown FIG. 1, the section being taken along the major longitudinal axis of the instrument, and showing the instrument prepared for insertion into the patient's abdomen with the rod advanced to the distal end of its range of movement with respect to the sleeve.

The instrument 1 is prepared for use by advancing the rod 3 distally within the sleeve 2 until the screw 13 abuts the distal end of the slot 12 to prevent further distal movement of the rod 3. A distal end portion of the rod 3 (of about 3.5 cm in length in the embodiment described) is thereby exposed beyond the distal end of the sleeve 2. A silicone rubber ring 26 (or other similar compatible material) is then placed around the exposed distal end portion of the rod 3 just beyond the ramp 10 at the distal end of the sleeve 2. The silicone ring 26 should be of at least 1 mm diameter when stretched; its inner diameter can range from 2 mm to 8 mm. Thus prepared as shown in FIG. 3, the instrument 1 is inserted into the patient's abdomen in the same manner as other known sterilization clip or ring applicators, typically using a trocar and canula.

Figure 4:
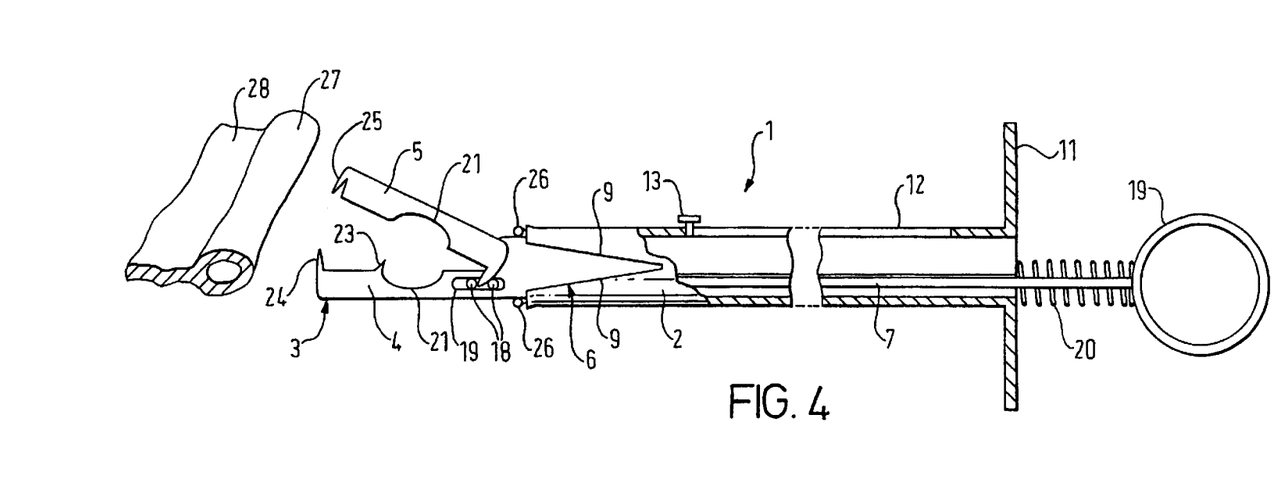
FIG. 4 is a side, elevational, partially schematic, partially sectional view of the instrument shown in FIG. 3, but showing the instrument in a patient's abdomen with jaws open to embrace an oviduct.

When the distal end of the instrument 1 nears the oviduct 27 as shown in FIG. 4 attached to the mesosalpinx 28, the actuating ring 19 at the proximal end of the actuating link 7 is squeezed towards the flange 11 at the proximal end of the sleeve 2 against the bias of the spring 20. Conveniently, the surgeon achieves this squeezing action by placing his or her thumb into the actuating ring 19 and by hooking the index and middle finger of the same hand around the flange 11 to press against the distal side of the flange 11. The proximal end of the sleeve 2 is held securely between the index and middle finger and the instrument 1 is therefore operated in the manner of a syringe. This action opens the jaws 4, 5 as shown in FIG. 4 to embrace the oviduct 27 between the opposed troughs 21 of the jaws 4, 5.

Figure 5:
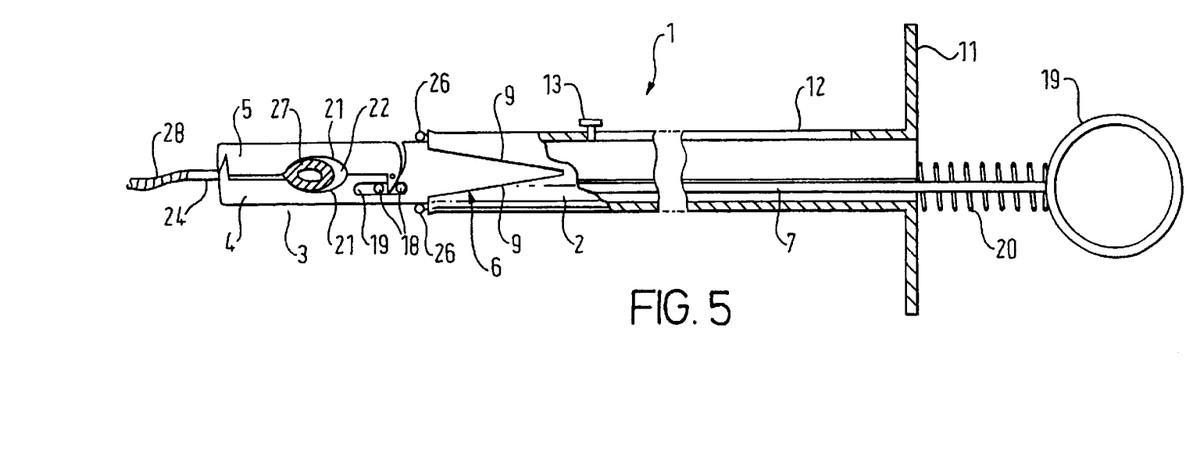
FIG. 5 is a side, elevational, partially schematic, partially sectional view of the instrument shown in FIG. 3, but showing the jaws closed around the oviduct and cutting through the mesosalpinx.

Once satisfied that the oviduct 27 is properly embraced between the opposed troughs 21 of the jaws 4, 5, the surgeon relaxes the pressure on the flange 11 and the actuating ring 19. This allows the bias force of the spring 20 to take over, which closes the jaws 4, 5 around the oviduct 27 with the oviduct 27 held in the receptacle defined between the closed jaws 4, 5. The closing movement of the jaws 4, 5 causes the recess 25 of the movable jaw 5 to receive the blade 24 of the fixed jaw 4, by doing so beginning to cut a slit in the mesosalpinx 28 to free the portion of the oviduct 27 held in the jaws 4, 5 from the mesosalpinx 28. This is shown in FIG. 5.

The small teeth or barbs 23 at the distal edge of the trough 21 in the fixed jaw 4 prevent the oviduct 27 from slipping back out from between the jaws 4, 5, and the bias force of the spring 20 holds the oviduct 27 firmly enough that the surgeon can move the instrument 1 to obtain the best possible view of the jaws 4, 5 to check their proper engagement with the oviduct 27. Even at this stage, the oviduct 27 can very easily be released by squeezing together the actuating ring 19 and flange 11 as before if the surgeon is not completely satisfied about any aspect of the procedure, whereupon the procedure can be repeated.

Figure 6:
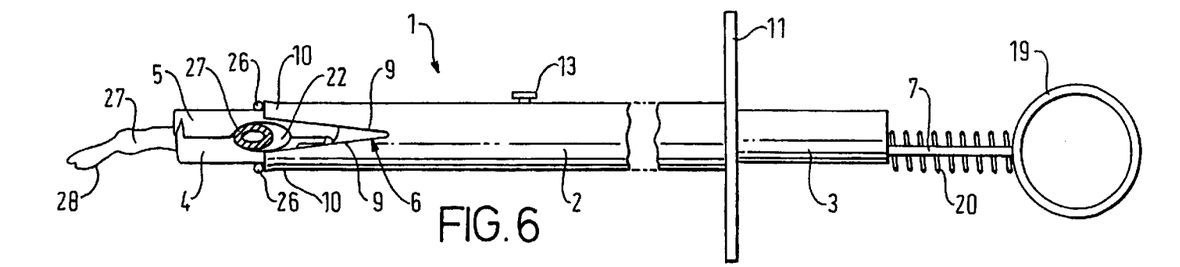
FIG. 6 is a side, elevational, partially schematic view of the instrument shown in FIG. 3, but showing the distal end portion of the rod being retracted into the distal end portion of the sleeve.

Once happy that the oviduct 27 is properly held within the receptacle 22 defined between the opposed jaws 4, 5, then the surgeon reverses the above squeezing action by pulling apart the flange 11 of the sleeve 2 and the actuating ring 19 of the actuating link 7. This manoeuvre retracts the distal end portion of the rod 3 into the sleeve 2 as shown in FIG. 6, effectively causing the ramp 10 at the proximal end of the sleeve 2 to push the silicone ring 26 over the closed jaws 4, 5 including the oviduct 27 grasped therein, which overhangs each side of the receptacle in the closed jaws 4, 5. The teeth or barbs 23 help to keep the oviduct 27 snugly in the receptacle 22 during this movement, aided by the proximal movement of the actuating link 7 with respect to the rod 3 that adds to the bias force of the spring 20 to pull the jaws 4, 5 tightly shut. The proximal movement of the rod 3 into the sleeve 2 as the sleeve 2 closely surrounds the closed jaws 4, 5 adds further to the bias force of the spring 20 to secure the immobility of the oviduct 27 in the receptacle 22. The increased closing force on the jaws 4, 5 also forces the blade 24 into the recess 25 and so completes the slit in the mesosalpinx 28.

Figure 7:
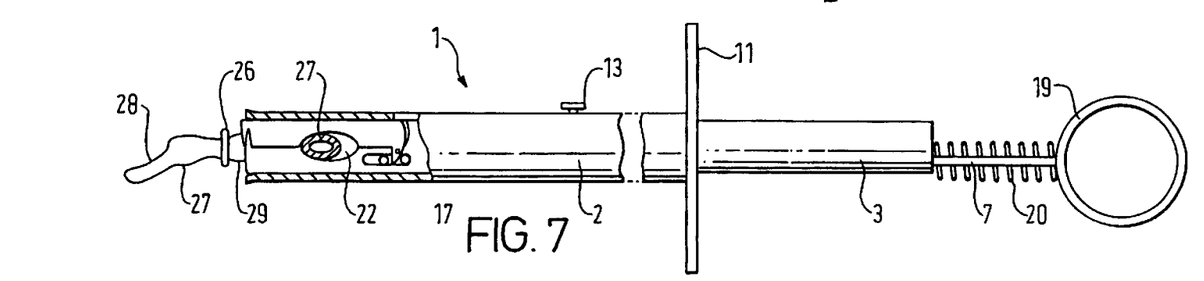
FIG. 7 is a side, elevational, partially schematic view of the instrument shown in FIG. 1, but showing the distal end portion of the rod further retracted into the distal end portion of the sleeve, to the extent that an occluding ring carried by the rod has slipped onto the neck of a loop in the oviduct and the oviduct is about to be cut with further retraction of the rod.
Figure 8:
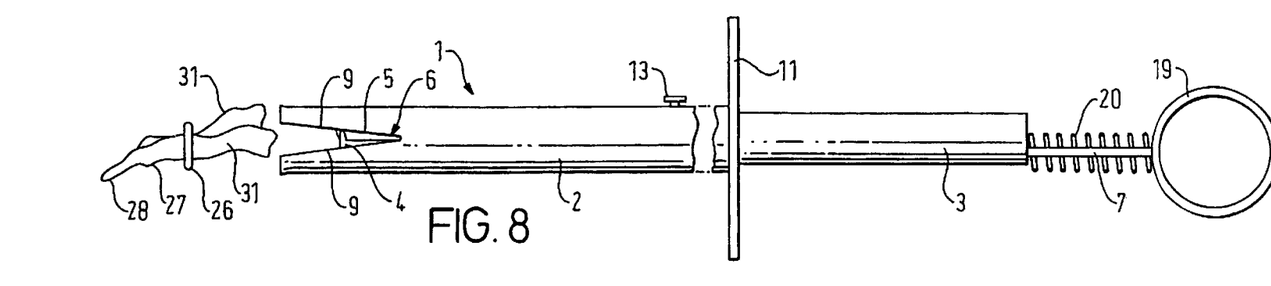
FIG. 8 is a side, elevational, partially schematic view of the instrument shown in FIG. 3, but showing the rod fully retracted into the distal end portion of the sleeve to cut the oviduct at the sides of the rod.
Figure 9:
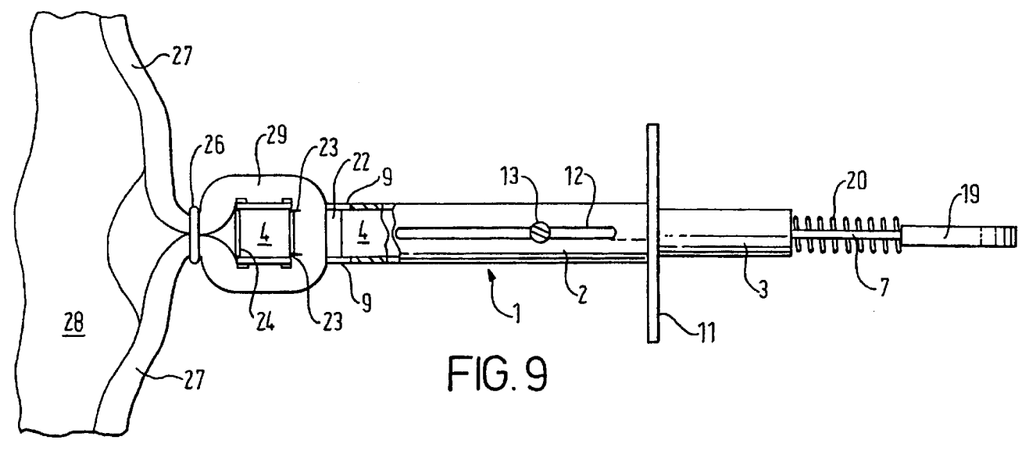
FIG. 9 is a side, elevational, partially schematic, partially sectional view of the instrument shown in FIG. 7, with the loop in the oviduct at the pre-cutting point shown in FIG. 7.
Figure 10:
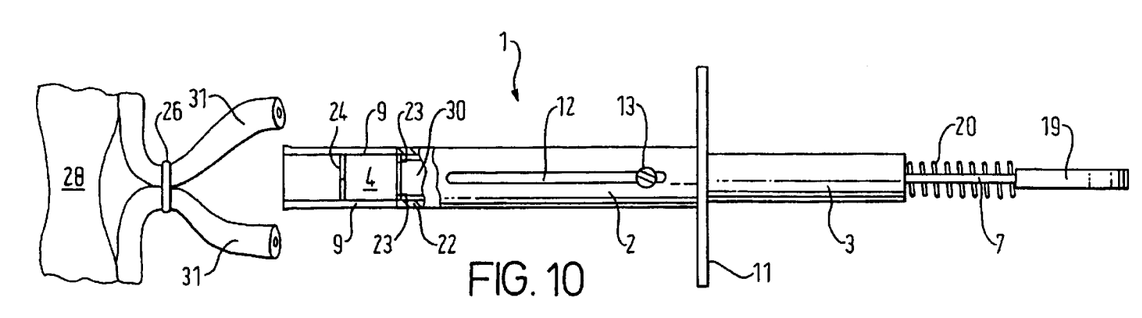
FIG. 10 is a side, elevational, partially schematic, partially sectional view of the instrument shown in FIG. 9, with the oviduct cut.

As the silicone ring 26 is pushed further along the closed jaws 4, 5 with continued retraction of the rod 3 into the sleeve 2, the ring 26 eventually slides off the distal extremity of the closed jaws 4, 5 as shown in FIGS. 7 and 9 to grip and occlude the neck of a loop 29 formed in the oviduct 27. Even at this very late stage, the surgeon can stop the procedure without any harm being done if he or she is not completely happy about everything. However, once the silicone ring 26 has tied off an appropriate loop 29 in the oviduct 27 and the surgeon is fully satisfied, further retraction of the rod 3 into the sleeve 2 draws the overhanging portions of the oviduct 27 into the cut-outs 6 in the distal end of the sleeve 2, thereby cutting the oviduct 27 on both sides of the rod 3 where the rod slides past the cutting edges 9 of the cut-outs 6. This situation is shown in FIGS. 8 and 10. Further retraction of the rod 3 into the sleeve 2 is unnecessary and so is prevented by abutment of the screw 13 with the proximal end of the slot 12.

Accordingly, by the end of the procedure, a 5 mm full circumferential biopsy 30 of the oviduct 27 is left in the receptacle 22 for recovery, safe keeping and histological analysis when the instrument 1 is removed from the patient's abdomen, confirming to surgeon and patient alike that the sterilization procedure was performed properly. The invention thereby provides for proper and convenient documentation to protect the surgeon and the patient, by avoiding litigation against the surgeon if the procedure was performed properly or by confirming the surgeon's negligence if the procedure was not performed properly. It is notable that the invention beneficially employs a biopsy excised from a segment of the oviduct that, after the Falope ring sterilization procedure, is simply left in the abdomen to slough away.

Of course, it is much better if an improper sterilization procedure is detected and remedied before it becomes a bigger problem for the patient and the surgeon. The invention allows for immediate examination of the biopsy 30 to detect such problems at the earliest possible stage.

In this example, the 5 mm biopsy 30 has been removed from the middle of a 2.5 cm loop 29 formed in the oviduct 27, thus leaving 1 cm stumps 31 of oviduct 27 beyond the occluding ring 26 on each side of the biopsy gap. The substantial length of these stumps 31 helps to retain the ring 26 on the oviduct 27.

Naturally, it is important that the instrument 1 is precisely engineered and particularly that the distal end portion of the rod 3 is as smooth as possible. This ensures that there are no gaps for the silicone ring 26 to jam into or sharp edges that might cut the ring 26 while it traverses the length of the jaws 4, 5 in use as described above.

It will be apparent to those skilled in the art that the sterilization biopsy procedure described above is very simple and does not greatly deviate in principle from techniques that are already in use and that are of proven efficacy, reliability and safety. The procedure is particularly akin to applying a Falope ring, which is generally accepted to be a safe, simple and reliable sterilization technique.

The essential familiarity of the procedure is an important factor in its acceptance among gynaecologists and obstetricians and uses their existing skills, much to the benefit of quality. It is well known and accepted that the physician's experience, or lack of it, is a major factor in sterilization failure rate, and that a physician skilled in a particular sterilization technique is likely to have a lower failure rate by continuing with that technique, or a development of it, than by changing to a wholly unfamiliar technique.

If anything, however, the instrument of the invention is superior to the Falope ring applicator. For example, the significant distance of the troughs 21 from the tip of the instrument (in this example, 1 cm) ensures a good uniform loop formation during every application. Also, the narrow tube of the Falope ring applicator (typically just 5 mm in diameter) sometimes does not accommodate the loop. This will result in the oviduct being severed or a small, inefficient and ineffective loop being formed. The commonest cause of such a failure is a thick oviduct, as will be encountered from time to time. The instrument of the invention can accommodate a 1 cm diameter oviduct easily, which is a great advantage over the Falope ring applicator and all other sterilization clip applicators. Further, the possibility of injury to other structures from sharp edges and from migration caused by the ring as compared to clips, is non-existent.

It is also believed that the occluded and cut oviduct left after the above procedure would tend to demonstrate a lower sterilization failure rate than a merely occluded oviduct, as is implied by the CREST study (the US Collaborative Review of Sterilization).

Many variations are possible within the inventive concept. For example, it is believed that the simplicity of the instrument makes it feasible for its parts to be made of disposable materials. In that case, the instrument suitably comes from the factory in a sterile pack, already assembled with the silicone ring already in place for use. Failing that, then silicone rings could be supplied separately with a cone, the base of which fits snugly over the jaws so that a ring can be pushed up the outer inclined surface of the cone and over the jaws to its resting place against the distal end of the sleeve. Similar means are already in use with Falope ring applicators.

In the broadest expressions of the invention, means other than a ring can be used to occlude the oviduct. For example, other embodiments are envisaged using V shaped clips or rectangular clips where the oviduct biopsy is cut out between the arms of the V or within the perimeter of the rectangle. A laparoscopic tying procedure is also contemplated, involving removal of the biopsy between the ties.

Similarly, various biopsy cutting techniques are contemplated whereby the clip itself could clip the oviduct and cut the biopsy at the same time, i.e. a cutting clip. Alternatively, a clip could be applied and the biopsy removed by a guillotine effect.

Aspects of the invention relate to a non-slip clip or ring, which once applied to the oviduct will not slip even if the oviduct is cut right beside the clip or ring. This non-slip characteristic is achieved by altering the configuration of the clips or rings used.

Figure 11A:
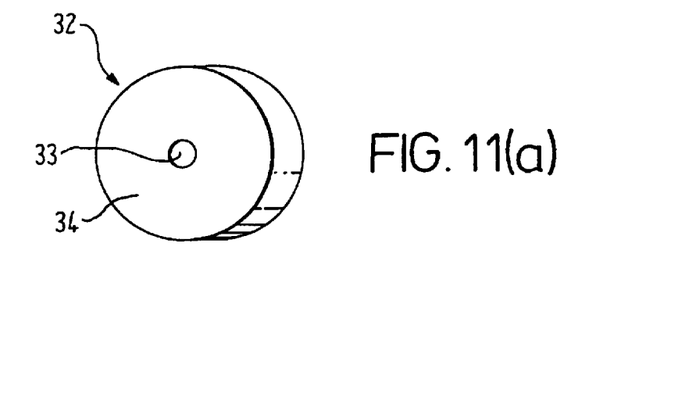
FIG. 11a is a front, perspective view of an occluding ring for use in the instrument of the present invention.
Figure 11B:
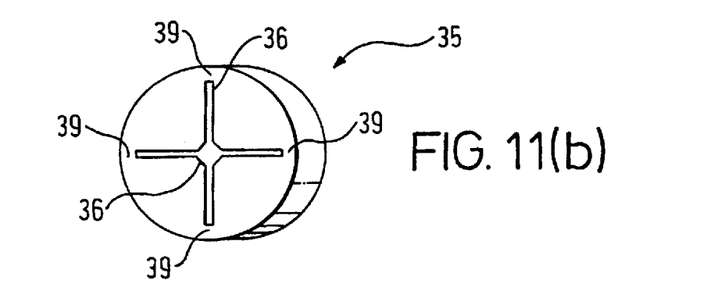
FIG. 11b is a front, perspective view of another occluding ring for use in the instrument of the present invention.
Figure 11C:
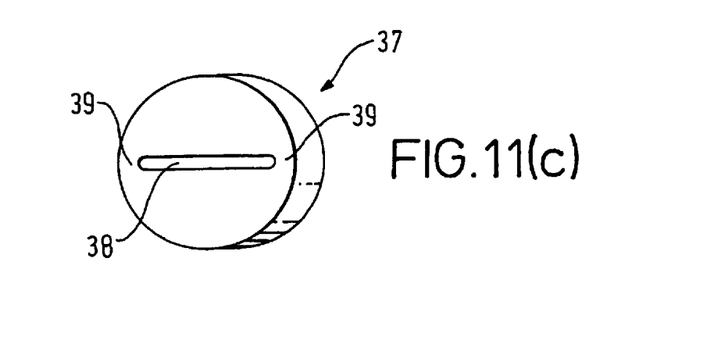
FIG. 11c is a front, perspective view of yet another occluding ring for use in the instrument of the present invention.

FIGS. 11(a), 11(b) and 11(c) illustrate possible clip or ring variants within the inventive concept. The clip or ring 32 of FIG. 11(a) has a small central opening 33 defining a very thick wall 34, that when stretched around an oviduct will apply strong occlusive compression to the oviduct. The clip or ring 35 of FIG. 11(b) has symmetrically-intersecting orthogonally disposed slits 36 defining a cross-shaped central opening. The clip or ring 37 of FIG. 11(c) is akin to that of FIG. 11(b) but has just one slit 38 defining a rectilinear central opening. It will be noted that the wall portions 39 at the end of the slits 36, 38 of FIGS. 11(b) and 11(c) are relatively thin, making it easier to stretch the clip or ring 35, 37 during its application to an oviduct, but that the central opening remains relatively small so that the clip or ring 35, 37 still applies strong occlusive compression to the oviduct and grips the oviduct securely.

This specification therefore demonstrates that there are many ways in which laparoscopic sterilization can be performed with full circumference biopsy excision of the oviduct. Accordingly, reference should be made to the accompanying claims and to other general statements herein, rather than to the foregoing specific description, as indicating the scope of the invention.

What is claimed is:

1. A laparoscopic sterilization instrument comprising:
an elongate rod and an elongate sleeve defining longitudinal axes and distal and proximal ends, the rod being movable distally and proximally within the sleeve and having gripping means for gripping a patient's oviduct;
excision means for excising a portion of the oviduct;
a receptacle associated with the rod for holding the excised oviduct portion until the instrument has been withdrawn from the patient's abdomen; and
wherein the excision means comprises at least one excision blade associated with the distal end of the sleeve and operates as the rod is moved proximally within the sleeve while gripping the oviduct, thus moving the gripped oviduct across the excision blade.

2. The instrument of claim 1, wherein the excision blade is defined by at least one sharp-edged cut-out in the distal end of the sleeve.

3. The instrument of claim 1, wherein means attached to one of said rod and sleeve and co-operable with the other of said rod and sleeve limits relative movement of the rod and sleeve.

4. The instrument of claim 1, further including application means for applying an occlusive device to the oviduct.

5. The instrument of claim 4, wherein the occlusive device is a clip or ring.

6. The instrument of claim 5, wherein the occlusive device is a ring held on a first part of the instrument and the application means operates by relative movement of a second part of the instrument to move the ring off the first part and onto the oviduct.

7. The instrument of claim 6, wherein the first part is the rod, the second part is the sleeve and a shoulder or ramp on the distal end of the sleeve abuts the ring to force the ring off the distal end of the rod during proximal movement of the rod relative to the sleeve.

8. The instrument of claim 4, and being operable to work the excision means and the application means in a single action.

9. The instrument of claim 8, wherein the application means operates before the excision means during said action.

10. The instrument of claim 1, wherein the receptacle is disposed transversely with respect to the longitudinal axis of the rod.

11. The instrument of claim 10, wherein the receptacle is defined between co-operating formations in opposed jaws at the distal end of the rod.

12. The instrument of claim 11, wherein the formations are troughs extending across the jaws that co-operate when the jaws are closed to define the receptacle.

13. The instrument of claim 12, wherein barb or tooth means are associated with at least one trough, and are adapted to resist removal of the oviduct from the receptacle or the trough.

14. The instrument of claim 12, wherein the troughs are separated from the distal extremity of the jaw with which the trough is associated.

15. The instrument of claim 14, wherein the separation between the trough and the distal extremity of the jaw is at least 1 cm.

16. The instrument of claim 12, wherein the length of each trough is at least 5 mm.

17. The instrument of claim 11, wherein blade means are associated with the jaws and are disposed distally with respect to the receptacle, the blade means being operable on closure of the jaws to cut the mesosalpinx.

18. The instrument of claim 17, wherein the blade means comprises at least one blade on one jaw, the blade being disposed transversely with respect to the longitudinal axis of the instrument, and means on the other jaw co-operable with that blade.

19. The instrument of claim 11, wherein the jaws are openable by an actuating link operable from the proximal end of the instrument.

20. The instrument of claim 19, wherein the actuating link acts on a movable jaw to which a fixed jaw is opposed.

21. The instrument of claim 19, wherein the jaws are openable by distal movement of the actuating link.

22. The instrument of claim 19, wherein the jaws are closable by proximal movement of the actuating link.

23. The instrument of claim 22, wherein continued proximal movement of the actuating link operates the excision means to excise the portion of oviduct held by the receptacle in the jaws.

24. The instrument of claim 19 including manipulation means that comprise means on the actuating link adapted for co-operation with the operator's thumb and means on an opposed part of the instrument adapted for co-operation with fingers of the operator's same hand.

25. The instrument of claim 24, wherein the manipulation means comprises a ring on the actuating link and a flange on the opposed part of the instrument.

26. The instrument of claim 11, wherein the jaws are biased shut by spring means.

27. The instrument of claim 26, wherein the jaws are openable by an actuating link operable from the proximal end of the instrument, and wherein the spring means biases the actuating link proximally.

28. The instrument of claim 1, being supplied in a sterile pack with an occlusive device already fitted to the instrument.

29. The instrument of claim 1, and being adapted for single use only.

* * * * *